United States Patent [19]

Saji et al.

[11] Patent Number: 5,541,101

[45] Date of Patent: Jul. 30, 1996

[54] ANTI-OXYTOCIN RECEPTOR ANTIBODIES

[76] Inventors: Fumitaka Saji, 4-33-308, Uegahara Yonban-cho, Nishinomiya, Hyogo; Chihiro Azuma, 2-16, Higashi Tanabe, Higashi Sumiyoshi-ku, Osaka; Tadashi Kimura, 11-1-714, Shimizu, Suita, Osaka, all of Japan

[21] Appl. No.: 101,041

[22] Filed: Aug. 3, 1993

[30] Foreign Application Priority Data

Aug. 3, 1992 [JP] Japan ................................. 4-206854

[51] Int. Cl.$^6$ ............................ C12N 5/12; C07K 16/26; C07K 16/18; G01N 33/53

[52] U.S. Cl. ................. 435/240.27; 435/7.2; 435/70.21; 530/388.22; 530/387.1; 530/387.9; 530/388.24; 530/389.2; 530/391.1

[58] Field of Search .............................. 530/387.1, 387.9, 530/388.22, 388.24, 389.2, 391.1; 435/70.2, 70.21, 68.1, 240.27, 7.2

[56] References Cited

FOREIGN PATENT DOCUMENTS 0542424  5/1993  European Pat. Off. .
WO-A-8403564  9/1984  WIPO .

OTHER PUBLICATIONS

Kimura et al, "Structure and Expression of a Human Oxytocin Receptor", NATURE, vol. 356, 9 Apr. 1992, pp. 526–529, London, GB—Correction as published in NATURE, vol. 357, 14 May 1992.

Kimura et al, "Structure and Expression of a Human Oxytocin Receptor", NATURE, vol. 356, 9 Apr. 1992, pp. 526–529, London, GB.

*Primary Examiner*—Margaret Parr
*Assistant Examiner*—Susan A. Loring
*Attorney, Agent, or Firm*—Bradford E. Kile; Kevin M. O'Brien; Ruffin B. Cordell

[57] ABSTRACT

Anti-oxytocin receptor antibodies, which specifically bind to the extracellular or intracellular region of an oxytocin receptor, hybridomas which produce said antibodies, and methods for the production of anti-oxytocin receptor antibodies are taught. These antibodies are useful for the immunodetection and immunopurification of oxytocin receptor polypeptides.

10 Claims, 6 Drawing Sheets

This is a micrograph (magnified 100x) of the results of immune staining of COS1 cells with recombinant DNA introduced using the monoclonal antibodies of Example 1 obtained by immunization with a combination of KLH and the polypeptide represented in Sequence No. 1.

This is a micrograph (magnified 100x) of the results of immune staining of COS1 cells without recombinant DNA introduced using the monoclonal antibodies of Example 1 obtained by immunization with a combination of KLH and the polypeptide represented in Sequence No. 1.

This is a micrograph (magnified 200x) of the results of immune staining of COS1 cells with recombinant DNA introduced using the polyclonal antibodies of Example 2 obtained by immunization with a combination of OVA and the polypeptide represented in Sequence No. 2.

This is a micrograph (magnified 200x) of the results of immune staining of COS1 cells with recombinant DNA introduced using the polyclonal antibodies of Example 2 obtained by immunization with OVA alone.

This is a micrograph (magnified 200x) of the results of immunohistological staining of human endometrial tissue using the polyclonal antibodies of Example 3 obtained by immunization with a combination of OVA and the polypeptide represented in Sequence No. 1.

This is a micrograph (magnified 200x) of the results of immunohistological staining of human endometrial tissue using the polyclonal antibodies of Example 3 obtained by immunization with OVA alone.

ANTI-OXYTOCIN RECEPTOR ANTIBODIES

FIELDS OF INDUSTRIAL USE

The present invention relates to antibodies which recognize and specifically bind to a receptor for a posterior pituitary hormone, oxytocin, hybridomas which secrete such antibodies, methods for their production, and methods of use of said antibodies for the detection and purification of said receptors.

BACKGROUND OF THE INVENTION

There is strong support for the action of oxytocin as a physiological initiator of delivery in numerous species of mammals, including humans, but the mechanism by which oxytocin accelerates contraction of uterine muscle has not yet been clarified in sufficient detail. An analysis of the diverse research conducted recently on the mechanism of this action indicates that oxytocin manifests this effect in part by inducing direct contractions of the tunica muscularis of the uterus and in part by increasing the synthesis and release of contractile prostaglandins from the endometrium and deciduous membrane. Moreover, initiation of the process that leads to delivery is considered attributable to increased sensitivity of uterine muscle to oxytocin; i.e., initiation of the process leading to delivery is partially attributable to an increase in oxytocin receptors in uterine muscle.

The management of premature birth is a vital issue in the field of obstetrics. It is known that there is an increased number of oxytocin receptors in cases of premature birth or imminent abortion. Moreover, in the clinical setting, there is a substantial need for the capability to predict premature birth by measuring the expression level of oxytocin receptors and for developing drugs to suppress labor pains in premature birth. Oxytocin is also known to have lactogenic and hypertensive effects.

However, the mode of expression of oxytocin receptors in target tissues remains unclear, so these actions are not yet understood in sufficient detail. Moreover, with regard to another aspect of oxytocin, there are reports that levels of the substance in the blood are elevated in males at the time of ejaculation, and that oxytocin receptors are expressed in rat hippocampus tissue. However, the series of biological responses between oxytocin and oxytocin receptors has not yet been fully explained, and further clarification is needed in this area.

With respect to the above clinical and research requirements, one possibility is the use of anti-oxytocin receptor antibodies that specifically binds oxytocin receptors for the immunodetection of such oxytocin receptors. Recently, Kimura et al. cloned the cDNA of oxytocin receptors (Nature, 356, 526–529 (1992)) and clarified its primary structure. Based on this primary structure, these receptors were presumed to have the sevenfold-membrane-penetration-type secondary structure typical of G-protein-binding-type receptors. However, this reference did not teach the production of antibodies which specifically bind to the oxytocin receptor.

As discussed, the development of anti-oxytocin receptor antibodies is desirable for the purification and identification of recombinant oxytocin receptors, as well as for the rapid detection and identification of oxytocin receptors present in oxytocin-receptor-manifesting tissues.

However, there have as of yet, been no reports on antibodies which specifically bind to oxytocin receptors. Accordingly, the object of the present invention is to provide antibodies which specifically bind to oxytocin receptors.

OBJECTS OF THE INVENTION

In order to achieve the above object, the present invention is directed to anti-oxytocin receptor antibodies which specifically bind oxytocin receptors, in particular human oxytocin receptors, or fragments thereof.

Another object of the invention is the production of hybridomas which secrete monoclonal antibodies which specifically bind oxytocin receptors, or to fragments thereof.

Still another object of the invention is to provide methods for the preparation of hybridomas that secrete such antibodies, wherein mammals are immunized with human oxytocin receptor polypeptides or fragments thereof comprising at least six amino acids, and which polypeptides may be conjugated to macromolecular immunogenic carrier moieties, immunocytes harvested from said mammals, said immunocytes fused with myeloma cells, and hybridomas obtained which secrete antibodies that specifically bind to oxytocin receptors, in particular, human oxytocin receptors, or fragments thereof.

Still another object of the invention is to provide methods for the production of anti-human oxytocin receptor binding monoclonal antibodies in which the aforementioned hybridomas are cultured under conditions suitable for expression of antibodies and monoclonal antibodies capable of specifically binding oxytocin receptors, or fragments thereof, are harvested from said culture.

Still yet another object of the invention is to provide methods for the production of anti-human oxytocin receptor polyclonal antibodies in wherein mammals or chickens are immunized with human oxytocin receptor polypeptides, or fragments thereof comprising at least six amino acids and which polypeptides may be conjugated to macromolecular immunogenic moities, and polyclonal antibodies which specifically bind human oxytocin receptors are then harvested from said serum or egg yolks obtained from said immunized mammals or chickens.

Still another object of the invention is to provide specific polypeptides corresponding to the oxytocin receptor which may be used to produce anti-oxytocin receptor antibodies or as oxytocin receptor agonists and antagonists.

Yet another object of the invention is to provide a method of using antibodies which specifically bind to oxytocin receptor polypeptides, or fragments thereof, to immunodetect or immunopurify oxytocin receptor polypeptides, or fragments thereof.

The file of this patent contains at least one drawing executed in color. Copies of this patent with color drawing(s) will be provided to the Patent and Trademark Office upon request and payment of the necessary fee.

Figure 1:
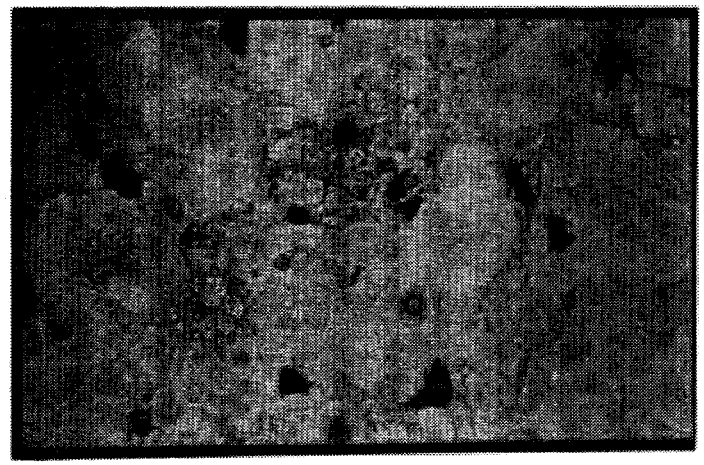
FIG. 1

This is a sketch of a micrograph (magnified 100×) of the results of immune staining of COS1 cells with recombinant DNA introduced using the monoclonal antibodies of Example 1 obtained by immunization with a combination of KLH and the polypeptide represented in Sequence No. 1.

FIG. 2

This is a sketch of a micrograph (magnified 100×) of the results of immune staining of COS1 cells without recombinant DNA introduced using the monoclonal antibodies of Example 1 obtained by immunization with a combination of KLH and the polypeptide represented in Sequence No. 1.

FIG. 3

This is a sketch of a micrograph (magnified 200×) of the results of immune staining of COS1 cells with recombinant DNA introduced using the polyclonal antibodies of Example 2 obtained by immunization with a combination of OVA and the polypeptide represented in Sequence No. 7.

FIG. 4

This is a sketch of a micrograph (magnified 200×) of the results of immune staining of COS1 cells with recombinant DNA introduced using the polyclonal antibodies of Example 2 obtained by immunization with OVA alone.

FIG. 5

This is a sketch of a micrograph (magnified 200×) of the results of immunohistological staining of human endometrial tissue using the polyclonal antibodies of Example 3 obtained by immunization with a combination of OVA and the polypeptide represented in Sequence No. 1.

FIG. 6

This is a sketch of a micrograph (magnified 200×) of the results of immunohistological staining of human endometrial tissue using the polyclonal antibodies of Example 3 obtained by immunization with OVA alone.

DESCRIPTION OF THE INVENTION

The present invention relates to anti-oxytocin receptor antibodies which specifically bind to an epitope comprised in either the extracellular or intracellular region of an oxytocin receptor. In the preferred embodiments the subject antibodies will specifically bind to the human oxytocin receptor.

The present invention is further directed to anti-oxytocin receptor antibodies which specifically bind to a polypeptide corresponding to the extracellular region of an oxytocin receptor. More specifically, the invention is directed to antibodies which specifically to an epitope contained in the amino acid sequence represented in Sequence No. 1 wherein said epitopes comprise at least six contiguous amino acids of Sequence No. 1.

The invention is further directed to anti-oxytocin receptor antibodies which specifically bind to a polypeptide corresponding to the intracellular region of an oxytocin receptor. Preferably, such antibodies will bind to a polypeptide corresponding to Sequence No. 7 or a fragment thereof, comprising at least six contiguous amino acids of Sequence No. 7.

The invention is also directed to anti-oxytocin receptor antibodies which specifically bind to an epitope contained in any one of the amino acid sequences set forth in Sequence No.'s 2–6, or a fragment thereof, having at least six contiguous amino acids of said sequences.

The present invention is also directed to methods for producing anti-oxytocin receptor antibodies comprising fusing myeloma cells with mammalian spleen cells which have been obtained from hosts having been immunized with a polypeptide corresponding to the extracellular region of an oxytocin receptor. In the preferred embodiments, such polypeptides will comprise an epitope contained in the amino acid sequence represented in Sequence No. 1, or a fragment thereof which comprises at least six contiguous amino acids of said sequence. The fused cells are then cultured under conditions which result in the production of antibodies which specifically bind to a polypeptide corresponding to the extracellular region of the oxytocin receptor, and more preferably bind to the polypeptide corresponding to the amino acid sequence represented in Sequence No. 1 or a fragment thereof comprising at least six contiguous amino acids of said sequence, and the antibodies are then harvested.

The invention is still further directed to methods for producing anti-oxytocin receptor antibodies comprising obtaining mammalian serum or chicken egg yolks from hosts having been immunized with a polypeptide corresponding to the extracellular region of an oxytocin receptor, said polypeptide preferably having the amino acid sequence represented in Sequence No. 1 or a fragment thereof comprising at least six contiguous amino acids of said sequence, purifying said serum or chicken egg yolks obtained from said immunized hosts and harvesting the resulting anti-oxytocin receptor antibodies which specifically bind to a polypeptide epitope contained in the extracellular region of the oxytocin receptor, and which preferably bind to an epitope contained in a polypeptide having the sequence represented in Sequence No. 1 or a fragment thereof comprising at least six contiguous amino acids of said sequence.

The invention is still further directed to methods of producing anti-oxytocin receptor antibodies comprising fusing myeloma cells with mammalian spleen cells which have been obtained from hosts immunized with polypeptides corresponding to the intracellular region of an oxytocin receptor, preferably having the amino acid sequence represented in Sequence No. 7 or a fragment thereof comprising at least six contiguous amino acids, culturing the resulting fused hybridoma cells under conditions resulting in the production of anti-oxytocin antibodies, and harvesting the resulting anti-oxytocin receptor antibodies which specifically bind to an epitope contained in the intracellular region of an oxytocin receptor, and which preferably bind a region having the amino acid sequence represented in Sequence No. 7 or a fragment thereof comprising at least six contiguous amino acids of said sequence.

The invention is still further directed to a method of producing polyclonal anti-oxytocin receptor antibodies comprising obtaining mammalian serum or chicken egg yolks from hosts which have been immunized with a polypeptide corresponding to the intracellular region of an oxytocin receptor, preferably a polypeptide having the amino acid sequence represented in Sequence No. 7, or a fragment thereof comprising at least six contiguous amino acids, purifying the resulting serum or chicken egg yolks, and harvesting the resulting polyclonal anti-oxytocin receptor antibodies which specifically bind to a polypeptide corresponding to the intracellular region of an oxytocin receptor, and which preferably bind to a polypeptide having the amino acid sequence represented in Sequence No. 7 or a fragment thereof comprising at least six contiguous amino acids of said sequence.

The invention is also directed to a method of producing monoclonal anti-oxytocin receptor antibodies comprising fusing myeloma cells with mammalian spleen cells which have been obtained from hosts immunized with any one of the oxytocin receptor polypeptides having the amino acid sequence set forth in Sequence No.'s 2–6, or a fragment thereof, comprising at least six contiguous amino acids, culturing the resulting fused hybridoma cells under conditions resulting in the production of anti-oxytocin antibodies, and selecting and harvesting the resulting anti-oxytocin receptor antibodies which specifically bind to an epitope of an oxytocin receptor comprised in any one of the amino acid sequences represented in Sequence No.'s 2–6, or a fragment thereof comprising at least six contiguous amino acids.

The invention is also directed to a method of producing polyclonal anti-oxytocin receptor antibodies comprising obtaining mammalian serum or chicken egg yolks from hosts which have been immunized with a polypeptide having any of the amino acids sequences represented in Sequence No.'s 2–6, or a fragment thereof, comprising at least six contiguous amino acids, purifying the resulting serum or chicken egg yolks, and harvesting the resulting polyclonal anti-oxytocin receptor antibodies which specifically bind to a portion of an oxytocin receptor having the amino acid sequences represented in Sequence No.'s 3–7, or a fragment thereof, comprising at least six contiguous amino acids of any one of said sequences.

The invention is further directed to the use of antibodies which specifically bind to anti-oxytocin receptors, preferably polypeptides having the sequences set forth in Sequences No.'s 1–7 or fragments thereof comprising at least six contiguous amino acids for the immunodetection of oxytocin receptors in analytes.

The invention is still further directed to the use of such antibodies for the immunopurification of oxytocin receptors contained in analytes.

The invention is also directed to oxytocin receptor polypeptides having the sequences set forth in Sequence No.'s 1–7, or fragments thereof, comprising at least six amino acids which may be used as immunogens or as oxytocin receptor agonists and antagonists.

DETAILED DESCRIPTION OF THE INVENTION

The antibodies of the present invention include those which specifically bind to a polypeptide corresponding to the extracellular region of an oxytocin receptor or a polypeptide epitope comprised in such receptors comprising at least six contiguous amino acids. The invention is further directed to antibodies which specifically bind the intracellular region of an oxytocin receptor or an epitope contained in the intracellular region of said oxytocin receptor comprising at least six contiguous amino acid sequences of said intracellular region.

Specific examples of such polypeptides include the polypeptides of the first extracellular region and the third intracellular region of the human oxytocin receptor. In the preferred embodiments, these polypeptides will comprise the sequences set forth in Sequences No.'s 1–7, or fragments thereof comprising at least six contiguous amino acids.

The immunogens used to produce the antibodies of the subject invention will comprise polypeptides corresponding to the extracellular or intracellular region of the oxytocin receptor or fragments thereof comprising at least six contiguous amino acids. These polypeptides will preferably be bound to a macromolecular carder which enhances the immunogenic response to said polypeptides upon in vivo administration. Specific examples of such polypeptides include polypeptides obtained by chemical synthesis of part of the amino acid sequence corresponding to the cDNA translation region of the oxytocin receptors disclosed by Kimura et al as cited supra. Preferably, these polypeptides will comprise all or part of the extracellular or intracellular region of said receptors, and more preferably polypeptides corresponding to the first extracellular or third intracellular region of said receptors. Most preferably, these polypeptides will correspond to the amino acid sequences represented in Sequences No.'s 1–7, or fragments thereof comprising at least six contiguous amino acids.

As noted supra, these polypeptides will preferably be bound to a macromolecular carrier which enhances the immune (antibody) response to the polypeptide. Specific examples of such carriers include keyhole lipid hemocyanin (KLH) and ovalbumin (OVA). Moreover, all or part of the aforementioned oxytocin receptor cDNA may be inserted in an expression vector that comprises appropriate regulatory sequences (promoter, terminator, etc.) and this expression vector may be used to produce the resulting oxytocin receptor polypeptide in suitable transformed recombinant host cells. However, preferably, the oxytocin receptor polypeptides will be expressed in *E. coli* or in mammalian cells.

Any of these oxytocin polypeptides of sufficient size may be used as immunogens for the preparation of hybridomas which secrete monoclonal antibodies or the production of polyclonal antibodies which specifically bind to oxytocin receptors.

The preparation of hybridomas may be effected by known methods. For example, mammals such as mice may be immunized with any of the aforementioned immunogens, spleen cells removed from said immunized animals, and said spleen cells fused with myeloma cells by well known techniques. Hybridomas which secrete monoclonal antibodies capable of specifically binding to oxytocin receptors may then be cloned.

For example, monoclonal antibodies may be obtained by culturing the cloned hybridomas on an appropriate culture medium under conditions suitable for antibody expression and harvesting the monoclonal antibodies from the resulting culture supernatant. Another method of obtaining monoclonal antibodies will comprise culturing the aforementioned hybridomas in the peritoneal cavity of suitable animals and purifying and isolating the resulting antibodies from the ascites fluid. These methods are well known in the art.

Production of polyclonal antibodies which specifically bind oxytocin receptors will also be carried out by known methods, for example, by immunizing mice, rabbits, sheep, goats, chickens with the aforementioned immunogens and purifying the serum of these animals, or in the case of chickens, egg yolks to obtain such antibodies.

In the following, examples are provided in order to more particularly explain the present invention. However, the invention is not limited to these examples.

EXAMPLE 1

Preparation of Monoclonal Antibodies Against Human Oxytocin Receptors

In order to prepare mouse monoclonal antibodies which specifically bind to human oxytocin receptors, a peptide consisting of a cysteine residue added to the N terminal of the peptide represented in Sequence No. 1, which is composed of 19 amino acids and corresponds to part of the region presumed to be the first extracellular region, was synthesized. Using the method presented by Hashida et at. (*Journal of Applied Biochemistry*, 6, 56–63, 1984), this peptide was then bound to keyhole lipid hemocyanin (KLH, Calbiochem Co.) and chicken egg albumin (OVA), grade V (Ovalbumin, Sigma Corp.).

50 µg/0.1 ml of $H_2O$ (pure water) of the peptide-KLH conjugate was then subcutaneously injected into BALB/C mice, together with 0.1 ml of Freund's complete adjuvant (FCA, Difco Laboratories, Inc.) to induce an immunogenic (antibody) response. After 10 days, 5 µg/0.2 ml (pure water) of said peptide-KLH conjugate was administered into the peritoneal cavity to provide for additional immunogenic response, and after 3 days, spleen cells were taken from the mice.

These spleen cells were then fused by known methods using polyethylene glycol, with the myeloma cells P3X63Ag8U1 (Dainippon Pharmaceutical Co., Ltd.). Cloning was then performed using the limiting dilution analysis method.

Evaluation of the antibody titer of the cloned cells was performed using the common ELISA method, specifically by adding the hybridoma culture supernatant to a microtiter plate with the aforementioned peptide-OVA conjugate solidified on it, followed by a measurement of the amount of mouse antibodies which bound to the peptide-OVA conjugate following immune reaction.

A hybridoma producing antibodies that specifically bind to the peptide-OVA conjugate was then obtained and cultured in GIT culture medium (Nihon Seiyaku Co., Ltd.). These antibodies were then isolated and purified from the culture supernatant by salting out with ammonium sulfate.

The segment extending from the first BamHI recognition site upstream from the translation region of the plasmid pOTR (Kimura et al Nature, 356, 526–529, 1992) containing the cDNA encoding the aforementioned human oxytocin receptors to the first PstI recognition site downstream from the translation region was then cut, removed, and made into a smooth terminal by known methodology, and a recombinant DNA molecule containing this segment was introduced into the multi-cloning site of the mammalian cell expression vector pRc/CMV (Invitrogen Corporation, U.S.A.) and used to transform COS1 cells (Dainippon Pharmaceutical Co., Ltd.) by the common calcium phosphate method.

Confirmation of transient expression of human oxytocin receptors by the COS1 cells three days after transformation was effected by common immune staining using the antibodies obtained above (antibody concentration 10 μg/ml). Specifically, cells cultured on a glass slide were fixed for 10 minutes with acetic acid/methanol (1:3, V/V). In order to eliminate their intrinsic peroxidase activity, the cells were then treated for 30 minutes with methanol containing 0.3 % hydrogen peroxide, and ordinary immune staining was performed with the Vectastain™ ABC Kit (Vector Laboratories, Inc., U.S.A.), using the aforementioned monoclonal antibodies (antibody concentration 10 μm/ml) as primary antibodies.

Figure 2:
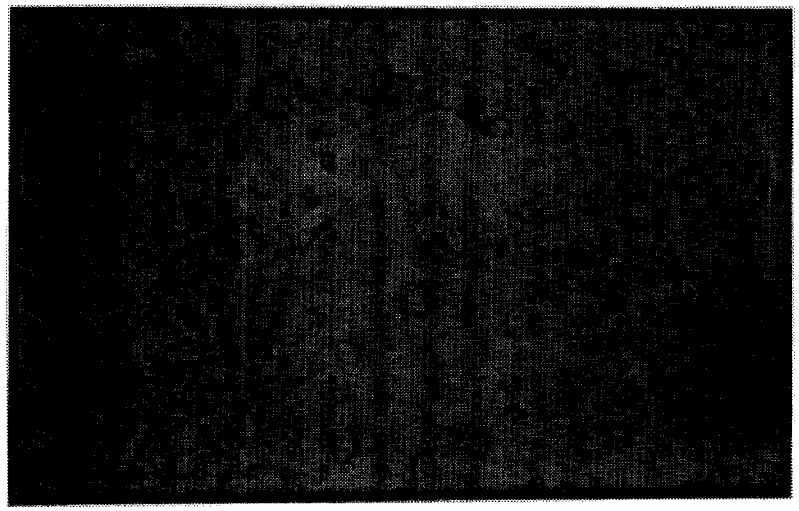

A mixture of equivalent amounts of 0.02 % hydrogen peroxide and 0.1% 3,3'-diaminobenzidine tetrahydrochloride (DAB) (Nakarai Kagaku Yakuhin K.K.) solution (0.1 M tris-buffer solution, prepared to a pH of 7.2) was used as a color substrate solution. As a result, it was possible to introduce the aforementioned recombinant DNA molecule and to detect antibodies (YA-1 antibodies), which with immune staining stain only those cells that express oxytocin receptors (see FIGS. 1 and 2). FIG. 1 is a sketch of a micrograph (magnified 100×) of the results of immune staining of COS1 cells with recombinant DNA introduced using the monoclonal antibodies of the present invention, and FIG. 2 is a sketch of a micrograph (magnified 100×) of the results of immune staining of COS1 cells without recombinant DNA introduced using the monoclonal antibodies of the present invention.

The micrograph represented in FIG. 1 shows that the COS1 cells that temporarily express oxytocin receptors (1) stained brown, while the COS1 cells which do not temporarily express oxytocin receptors (2) are not stained (transparent). Moreover, in the micrograph represented in FIG. 2, one can see that the COS1 cells which do not express oxytocin receptors (3) are not stained (transparent). The hybridoma that produces these antibodies was designated mouse/mouse hybridoma YA-1. This hybridoma YA-1 was deposited on May 7, 1995 with the National Institute of Bioscience and Human - Technology, Agency of Industrial Science and Technology, whose address is 1–3, Nigashi 1 chome, Tsububa-shi, Ibaraki-ken, 305 Japan, and has been accorded Accession No. BP-5095.

This deposit was made in accordance with the Budapest Treaty. Upon issuance of a patent to this application or an application which claims benefit to this application, all restrictions as to the availability of this hybridoma cell line will be irrevocably withdrawn.

EXAMPLE 2

Preparation of Polyclonal Antibodies Against Human Oxytocin Receptors

In order to prepare polyclonal antibodies which specifically bind to human oxytocin receptors, a peptide consisting of a cysteine residue added to the N terminal of the peptide represented in Sequence No. 7, which is composed of 15 amino acids and corresponds to part of the third intracellular region, was synthesized as an immunogen by a common method. As was the case in Example 1, this peptide was caused to bind to OVA (Sigma Corp.).

Approximately 0.5 mg/ml (pure water) of this peptide-OVA conjugate was administered to Japanese white rabbits together with 1 ml of Freund's complete adjuvant (Difco Laboratories, Inc.) for initial immunization. Six subsequent immunizations were performed once weekly thereafter (for a total of seven immunizations) with the same amount of peptide-OVA conjugate together with Freund's incomplete adjuvant (FIA, Difco Laboratories, Inc.), and whole blood samples were taken. The serum was isolated using a common method, and the serum obtained was subjected to affinity purification using a Protein A Sepharose CL-4B column (Pharmacia LKB Biotechnology).

Figure 3:
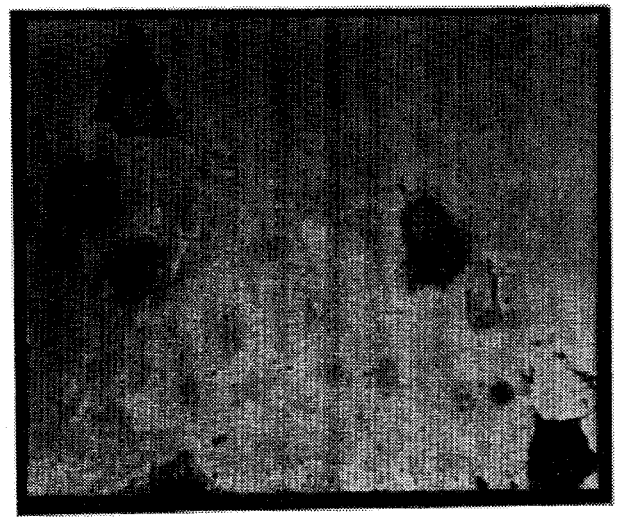
Figure 4:

FIGS. 3 and 4 show that the polyclonal antibodies produced in this manner specifically bind to oxytocin receptors. As was the case in Example 1, the mammalian cell expression vector pRc/CMV containing the cDNA encoding the human oxytocin receptors obtained in Example 1 was introduced into COS1 cells. With respect to its transient expression, ordinary immune staining was performed using the aforementioned antibodies (antibody concentration 10 μg/ml) and, as was the case in Example 1, a Vectastain ABC Kit (Vector Laboratories). A mixture of equivalent amounts of 0.02 % hydrogen peroxide and 0.1% DAB (Nakarai Kagaku Yakuhin K.K.) solution (0.1 M tris-buffer solution, adjusted to a pH of 7.2) was used as a color substrate solution. After this, ordinary hematoxylin staining (Mayer's hematoxylin, Takefu Kagaku Yakuhin K.K.) was performed. The results showed that when the aforementioned polyclonal antibodies were used, stained cells were observed (see FIG. 3), but with antibodies obtained by immunization with OVA alone, stained cells were not observed (see FIG. 4).

FIG. 3 is a sketch of a micrograph (magnified 200×) of the results of immune staining of COS1 cells expressing oxytocin receptors using the polyclonal antibodies of the present invention, and FIG. 4 is a sketch of a micrograph (magnified 200×) of the results of immune staining of COS1 cells expressing oxytocin receptors using antibodies obtained by immunization with OVA alone. The micrograph represented in FIG. 3 shows that the COS1 cells expressing oxytocin receptors (4) are stained brown by the antibodies of the present invention, while the micrograph represented in FIG. 4 shows that staining does not occur (transparent) with the antibodies obtained by immunization with OVA alone. Moreover, hematoxylin staining of the nuclei (See FIGS. 3 and 4, at 5, 6, and 9) of the COS1 cells produces a blue color.

EXAMPLE 3

Preparation of Polyclonal Antibodies Against Human Oxytocin Receptors

Using the peptide-OVA conjugate prepared in Example 1 as an immunogen, Japanese white rabbits were immunized by the same method as in Example 2, and the serum obtained was subjected to affinity purification using the Protein A Sepharose CL-4B column (Pharmacia LKB Biotechnology).

Human uterine muscle obtained by chance during the ovulation period (in the form of a pathology specimen from a patient who had to undergo a total hysterectomy due to a hysteromyoma) was rapidly frozen to −70° C. in liquid nitrogen. Frozen sections of this tissue were prepared using a cryostat (Tissue-Tek II™, Miles Co.), and ordinary immunohistological staining was performed.

Specifically, fragments adhering to the glass slide were fixed for 10 minutes with acetone, and in order to eliminate their intrinsic peroxidase activity, the fragments were then treated for 30 minutes with methanol containing 0.3 % hydrogen peroxide. After this, ordinary immunohistological staining was performed with the aforementioned polyclonal antibodies (antibody concentration 20 µg/ml) as primary antibodies, using the Vectastain ABC Kit (Vector Laboratories, Inc.). A mixture of equivalent amounts of 0.02% hydrogen peroxide and 0.1% DAB (Nakarai Kagaku Yakuhin K.K.) solution (0.1 M tris-buffer solution, adjusted to a pH of 7.2) was used as a color substrate solution.

Figure 5:
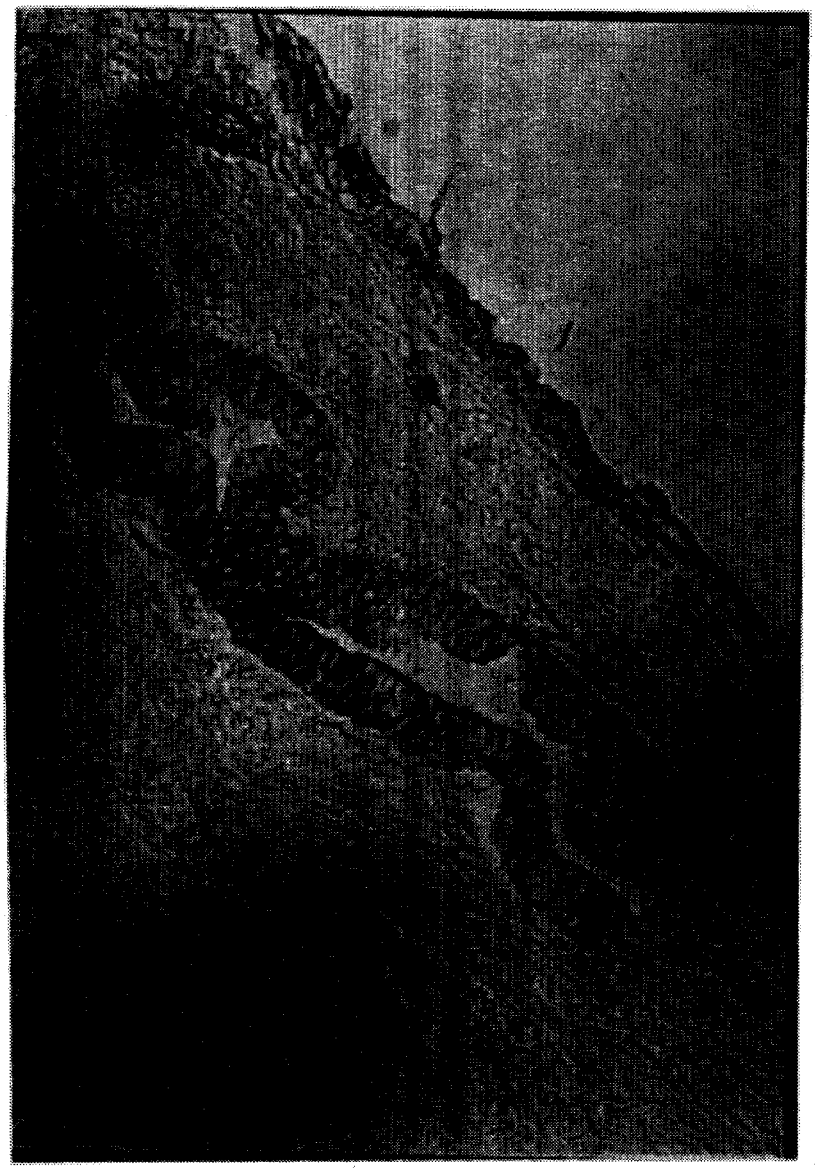
Figure 6:
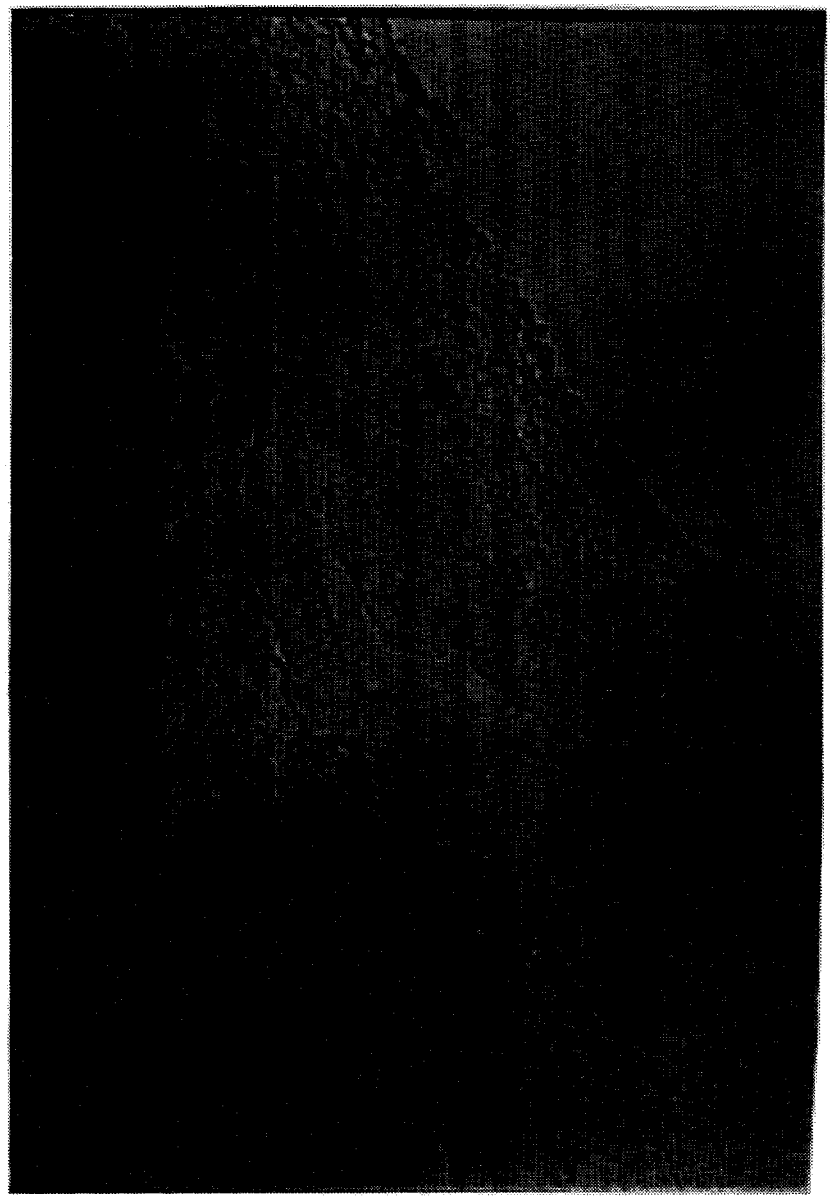

FIGS. 5 and 6 show that oxytocin receptors that are expressed in epithelial cells of the endometrium during the ovulation period were stained only when polyclonal antibodies prepared as described above were used as primary antibodies (see FIG. 5). FIG. 5 is a sketch of a micrograph (magnified 200×) of the results of immunohistological staining of human endometrial tissue using the polyclonal antibodies of the present invention, and FIG. 6 is a sketch of a micrograph (magnified 200×) of the results of immunohistological staining of antibodies obtained by immunization with OVA alone.

The micrograph represented in FIG. 5 shows that the endometrial epithelial cells (10, 11) were stained brown, while the endometrial interstitium (12) was not stained (transparent). Moreover, one can see from the micrograph represented in FIG. 6 that the endometrial epithelial cells (14, 15) were not stained (transparent).

EXAMPLE 4

Preparation of Polyclonal Antibodies Against the Extracellular Region of Human Oxytocin Receptors In order to prepare polyclonal antibodies which specifically bind to the extracellular region of human oxytocin receptors, peptides consisting of cysteine residue added to the N terminals of the peptides represented in Sequence Nos. 2 and 3, which are composed of amino acids corresponding to part of the first extracellular region, and to the N terminal of the peptide represented in Sequence No. 6, which is composed of amino acids corresponding to part of the fourth extracellular region (hereinafter called "Peptide 2," "Peptide 3," and "Peptide 6," respectively) were synthesized by a common method. As was the case in Example 1, 0.5 mg/ml (pure water) each of these peptides were caused to bind to OVA (Sigma Corp.), thus producing Peptide 2-OVA conjugate, Peptide 3-OVA conjugate, and Peptide 6-OVA conjugate. These peptide-OVA conjugates were used as immunogens to immunize Japanese white rabbits as described in Example 2, and the three types of serum thus obtained were subjected to affinity purification. "Polyclonal Antibody 2" was obtained from the serum obtained by using Peptide 2-OVA conjugate, "Polyclonal Antibody 3" was obtained from the serum obtained by using Peptide 3-OVA conjugate, and "Polyclonal Antibody 6" was obtained from the serum obtained by using Peptide 6-OVA conjugate. As was the case in Example 1, the aforementioned synthetic peptides were caused to bind to KLH (Calbiochem), producing, respectively, Peptide 2KLH conjugate, Peptide 3-KLH conjugate, and Peptide 6-KLH conjugate.

Next, the peptide represented in Sequence No. 4, which is composed of amino acids corresponding to part of the second extracellular region of human oxytocin receptors (hereinafter called "Peptide 4") and the peptide represented in Sequence No. 5, which is composed of amino acids corresponding to part of the third extracellular region (hereinafter called "Peptide 5") were synthesized by a common method. As was the case in Example 1, using the cysteine that is intrinsic in these synthetic peptides, Peptide 4-OVA conjugate and Peptide 5-OVA conjugate, prepared by binding the peptides to OVA, were each used in quantities of 0.5 mg/ml (pure water) as immunogens to immunize Japanese white rabbits as described in Example 2, and the two types of serum thus obtained were subjected to affinity purification. "Polyclonal Antibody 4" was obtained from the serum obtained by using Peptide 4-OVA conjugate, and "Polyclonal Antibody 5" was obtained from the serum obtained by using Peptide 5-OVA conjugate. Further, using the cysteine that is intrinsic in these synthetic peptides, these peptides were bound to KLH as described in Example 1, thus producing Peptide 4-KLH conjugate and Peptide 5-KLH conjugate. Table 1 shows that the polyclonal antibodies thus prepared binded specifically to polypeptides corresponding to the first through fourth extracellular regions of human oxytocin receptors. Specifically, the results of assaying the binding capacity of the aforementioned polyclonal antibodies using microtiter plates on which respective peptide-KLH conjugates and KLH were solidified indicate that Polyclonal Antibody 2 binds only to Peptide 2-KLH conjugate and Peptide 3-KLH conjugate. Similarly, Polyclonal Antibody 3 binds only to Peptide 2-KLH conjugate and Peptide 3-KLH conjugate. Also, Polyclonal Antibody 4, Polyclonal Antibody 5, and Polyclonal Antibody 6 bind only to Peptide 4-KLH conjugate, Peptide 5-KLH conjugate, and Peptide 6-KLH conjugate, respectively.

TABLE 1

| Solidifed Antigen | Polyclonal Antibody | | | | |
|---|---|---|---|---|---|
| | 2 | 3 | 4 | 5 | 6 |
| Peptide 2-KLH Conjugate | + | + | − | − | − |
| Peptide 3-KLH Conjugate | + | + | − | − | − |
| Peptide 4-KLH Conjugate | − | − | + | − | − |

TABLE 1-continued

| Solidifed Antigen | Polyclonal Antibody | | | | |
|---|---|---|---|---|---|
| | 2 | 3 | 4 | 5 | 6 |
| Peptide 5-KLH Conjugate | − | − | − | + | − |
| Peptide 6-KLH Conjugate | − | − | − | − | + |
| KLH | − | − | − | − | − |

+: Antibody binds to solidified antigen
−: Antibody does not bind to solidifed antigen

EXAMPLE 5

Method of Screening Anti-Oxytocin Receptor Antibodies Inhibiting the Binding Capacity of Oxytocin to Human Oxytocin Receptors In order to develop a screening method for anti-oxytocin receptor antibodies that inhibit the binding capacity of oxytocin to human oxytocin receptors, the recombinant DNA molecules prepared in Example 1 were introduced into HeLa cells using the ordinary calcium phosphate method. After introduction, clones were cultured in colonies in a culture medium supplemented with geneticin-sulfate (Wako Junyaku). The following binding experiment was performed in order to select oxytocin receptor-expressing strains from the clones, using 36.6 Ci/mmol (tyrosyl-2,6-$^3$H)- oxytocin (hereinafter called $^3$H-OT) (New England Nuclear Corp.): Dulbecco PBS(−)™ (Nissui Seiyaku) containing 0.1% EDTA was added to culture dishes containing the clones, reproduced by a common cell culture method. The dishes were allowed to stand at 37° C. for 20 minutes, after which the cells were removed from the culture dishes. The suspended cells were collected by centrifuging, washed in Dulbecco PBS(−), and were then re-collected by centrifuging. In order to measure the total amount of bound oxytocin, binding experiment buffer solution (50 mM tris (pH 7.6)), 5 mM manganese chloride, 150 mM NaCl, 200 μg/ml bovine serum albumin, 40 μg/ml bacitracin (Sigma Corp.), 4 μg/ml leupeptin (Sigma Corp), and 20 μg/ml chymostatin (Sigma Corp.), were prepared for a final concentration of 2×10$^5$ cells per 200 μl and 10 nM of $^3$H-OT. The mixture was incubated for 30 minutes at 30° C. Also, in order to measure the amount of nonspecific binding, samples were prepared with 2×10$^5$ cells in 200 μl of binding experiment buffer, for a final $^3$H-OT concentration of 10 nM, and for a final minimum concentration of 1 μM of oxytocin not labeled with $^3$H. The mixture was incubated under the same conditions as described above. Afterwards, the cells were filtered through GF/C glass-fiber filter paper (Whatman Corp.) and washed in chilled binding experiment buffer; the cells that remained on the filter paper were transferred to a Scintillator 299™ (Packard Instrument Corp.) and dissolved. The $^3$H level of the resulting sample was measured using Liquid Scintillation Analyzer (Packard Instrument Corp.). The amount of specific binding of oxytocin was determined by subtracting the amount of nonspecific binding from the amount of total binding. Clones showing a specific oxytocin binding amount of 10,000 cpm or greater per 2×10$^5$ cells were used in the following experiment:

For antibodies, Polyclonal Antibody 7, which was obtained in Example 2, and Polyclonal Antibody 4, which was obtained in Example 4, were used. The antibodies were added to the buffer solution, prepared with a concentration of 2×10$^5$ transformed cells per 200 μl of binding experiment buffer solution and with a final $^3$H-OT concentration of 10 nM. The results were final antibody concentrations of 0.02 μg/ml, 0.2 μg/ml, and 2.0 μg/ml. The mixtures were then incubated for 60 minutes at 30° C. In order to measure nonspecific binding, oxytocin with a concentration of 1 μM or greater was used as described above. Table 2 shows that the transformant used in this experiment can be used for the screening of anti-oxytocin receptor antibodies that inhibit the binding of oxytocin to human oxytocin receptors. Whereas Polyclonal Antibody 4 inhibited the binding of oxytocin to oxytocin receptors even at a concentration of 0.02 μg/ml, Polyclonal Antibody 7 did not exhibit any inhibition, even at a concentration of 2 μg/ml.

TABLE 2

| | Concentration (μg/ml) | Oxytocin Specific Binding Ratio |
|---|---|---|
| Polyclonal Antibody 4 | 0 | 100 |
| | 0.02 | 82 |
| | 0.2 | 70 |
| | 2.0 | 68 |
| Polyclonal antibody 7 | 0 | 100 |
| | 0.02 | 100 |
| | 0.2 | 100 |
| | 2.0 | 100 |

Utility of the Subject Invention

The antibodies of the present invention comprise those antibodies which specifically bind to the extracellular region of an oxytocin receptor and those which specifically bind to the intracellular region of an oxytocin receptor. These antibodies will include monoclonal antibodies, polyclonal antibodies, as well as antibodies obtained by recombinant methods, e.g., chimeric and single chain antibodies. Antibodies which bind to the extracellular region of the oxytocin receptor may be used as agents to inhibit the physiological activity of oxytocin in order to block specific binding with respect to oxytocin receptors, for instance, as agents which regulate the time of delivery, i.e., agents which inhibit labor pains in premature birth. Moreover, seeing as oxytocin receptors are believed to be receptors of the G-protein-binding type, antibodies which bind to the intracellular region of the oxytocin receptor may be used in the same way to inhibit oxytocin activity by blocking binding to G-protein receptors.

Of course, these antibodies may also be used in the fields of obstetrics and gynecology as reagents for immune staining of pathological tissues such as from the mammaries, uterine muscle, endometrium, deciduous membrane, amnion, and so forth. Moreover, seeing as proteins which can bind to oxytocin in the hippocampus tissue of rats are known to exist, these antibodies may also be used in neuroscientific research. By using the antibodies of the present invention, it is therefore possible to further clarify the mechanism of the series of biological responses between oxytocin and oxytocin receptors, a problem that has hitherto remained largely unsolved, and this should be an aid in the development of pharmaceuticals in this field.

Furthermore, with respect to the development of oxytocin antagonists, transformants can be obtained by introducing the oxytocin receptor cDNA disclosed by Kimura et al. (described above) or a fragment thereof, in an appropriate expression vector followed by phenotypic transformation of mammalian cells, and the resultant transformants can be used to screen for anti-oxytocin receptor antibodies that inhibit the binding of oxytocin to oxytocin receptors.

Additionally, the subject anti-oxytocin antibodies may be used for the immunodetection of oxytocin receptors in analytes using methods which are well known in the art, e.g., ELISA, radioimmunoassay, Western blotting, dot blotting, etc. These antibodies may be labelled and the resultant immune complexes may be directly detected, or immune complexes may be indirectly detected using labelled antibodies which specifically bind to the antibodies of the invention. Suitable labels are well known in the art and include e.g., fluorescent labels, radiolabels, enzyme labels, etc.

Still further, the antibodies of the present invention may be used for the immunopufification of oxytocin receptors from analytes. For example, the subject antibodies may be bound to a solid phase matrix or support which is then contacted with an analyte suspected to contain oxytocin receptor polypeptides, or fragments thereof.

While having described the subject invention in specific embodiments, it is evident that many alternatives, modifications and variations will be apparent to those skilled in the art in view of the foregoing description. Accordingly, the invention is intended to embrace all such alternatives, modifications, and variations in following with the broadest scope and spirit of the following claims.

What is claimed is:

1. An anti-oxytocin receptor antibody which specifically binds to an extracellular or intracellular region of an oxytocin receptor polypeptide having the amino acid sequence selected from those represented in Sequence Nos. 1 through 7 or a fragment of any of said receptor polypeptides.

2. The anti-oxytocin receptor antibody of claim 1 which antibody specifically binds to a polypeptide having the amino acid sequence represented in Sequence No. 1 or a fragment thereof comprising at least six contiguous amino acids of said sequence.

3. The anti-oxytocin receptor antibody of claim 1 which specifically binds to an intracellular region of an oxytocin receptor having the amino acid sequence represented in Sequence No. 7, or a fragment thereof comprising at least six contiguous amino acids.

4. A hybridoma which produces an anti-oxytocin receptor antibody according to claim 1.

5. The hybridoma of claim 4 wherein said antibody specifically binds to a polypeptide having the amino acid sequence in Sequence No. 1 or a fragment thereof comprising at least six contiguous amino acids of said sequence.

6. The hybridoma of claim 4 wherein said antibody specifically binds to a polypeptide having the amino acid sequence in Sequence No. 7 or a fragment thereof comprising at least six contiguous amino acids of said sequence.

7. Hybridoma YA-1 which has been deposited with the National Institute of Bioscience and has been accorded accession Number BP-5095.

8. The anti-oxytocin receptor antibody according to claim 1 which specifically binds to an epitope contained in any one of the oxytocin receptor polypeptides set forth in Sequence No.'s 2–6, or a fragment thereof comprising at least six contiguous amino acids.

9. A hybridoma which secretes a monoclonal antibody as set forth in claim 8 which specifically binds to an epitope contained in any of the oxytocin receptor polypeptides set forth in Sequence No.'s 2–6, or a fragment thereof comprising at least six contiguous amino acids.

10. The monoclonal antibody produced by the hybridoma of claim 7.

* * * * *

UNITED STATES PATENT AND TRADEMARK OFFICE
CERTIFICATE OF CORRECTION

PATENT NO. : 5,541,101
DATED : July 30, 1996
INVENTOR(S) : Fumitaka et al.

It is certified that error appears in the above-identified patent and that said Letters Patent is hereby corrected as shown below:

<u>Title page,</u>
Insert:

Item [73] Assignee: Rhoto Pharmaceutical Co., Ltd.
                        Osaka, Japan Signed and Sealed this Eighteenth Day of December, 2001

*Attest:*

*Attesting Officer*

JAMES E. ROGAN
*Director of the United States Patent and Trademark Office*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..19
        ( D ) OTHER INFORMATION: /note="Part of the first extracellular region of the oxytocin receptor."

( x i ) SEQUENCE DESCRIPTION: SEQ ID NO:1:

```
Met  Glu  Gly  Ala  Leu  Ala  Ala  Asn  Trp  Ser  Ala  Glu  Ala  Ala  Asn  Ala
 1                  5                        10                      15
Ser  Ala  Ala
```

( 2 ) INFORMATION FOR SEQ ID NO:2:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..19
        ( D ) OTHER INFORMATION: /note="Amino acids 14-32 of the oxytocin receptor polypeptide."

( x i ) SEQUENCE DESCRIPTION: SEQ ID NO:2:

```
Ala  Asn  Ala  Ser  Ala  Ala  Pro  Pro  Gly  Ala  Glu  Gly  Asn  Arg  Thr  Ala
 1                  5                        10                      15
Gly  Pro  Pro
```

( 2 ) INFORMATION FOR SEQ ID NO:3:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Peptide
    ( B ) LOCATION: 1..21
    ( D ) OTHER INFORMATION: /note="Amino acids 20-40 of the
        oxytocin receptor."

( x i ) SEQUENCE DESCRIPTION: SEQ ID NO:3:

```
Pro  Pro  Gly  Ala  Glu  Gly  Asn  Arg  Thr  Ala  Gly  Pro  Pro  Arg  Arg  Asn
1                  5                            10                           15

Glu  Ala  Leu  Ala  Arg
                20
```

( 2 ) INFORMATION FOR SEQ ID NO:4:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..18
        ( D ) OTHER INFORMATION: /note="Amino acids 102-119 of the
            oxytocin receptor polypeptide."

( x i ) SEQUENCE DESCRIPTION: SEQ ID NO:4:

```
Thr  Phe  Arg  Phe  Tyr  Gly  Pro  Asp  Leu  Leu  Cys  Arg  Leu  Val  Lys  Tyr
1                  5                            10                           15

Leu  Gln
```

( 2 ) INFORMATION FOR SEQ ID NO:5:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..19
        ( D ) OTHER INFORMATION: /note="Amino acids 176-194 of the
            oxytocin receptor polypeptide."

( x i ) SEQUENCE DESCRIPTION: SEQ ID NO:5:

```
Ser  Leu  Arg  Glu  Val  Ala  Asp  Glu  Val  Phe  Asp  Cys  Trp  Ala  Val  Phe
1                  5                            10                           15

Ile  Gln  Pro
```

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..12
        ( D ) OTHER INFORMATION: /note="Amino acids 298-309 of the oxytocin receptor polypeptide."

(x i) SEQUENCE DESCRIPTION: SEQ ID NO:6:

```
Ser Val Trp Asp Ala Asn Ala Pro Lys Glu Ala Ser
 1            5                   10
```

(2) INFORMATION FOR SEQ ID NO:7:

(i) SEQUENCE CHARACTERISTICS:
       (A) LENGTH: 15 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Peptide
       (B) LOCATION: 1..15
       (D) OTHER INFORMATION: /note="Part of the third
           intracellular region of the oxytocin receptor."

(xi) SEQUENCE DESCRIPTION: SEQ ID NO:7:

```
Ser Ser Val Lys Leu Ile Ser Lys Ala Lys Ile Arg Thr Val Lys
 1            5                   10                  15
```